United States Patent
Klemp

(12) 
(10) Patent No.: US 6,702,795 B2
(45) Date of Patent: Mar. 9, 2004

(54) DISPOSABLE ABSORBENT GARMENT HAVING STRETCHABLE SIDE WAIST REGIONS

(75) Inventor: Walter V. Klemp, Houston, TX (US)

(73) Assignee: Associated Hygienic Products LLC, Duluth, GA (US)

( * ) Notice: Subject to any disclaimer, the term of this patent is extended or adjusted under 35 U.S.C. 154(b) by 168 days.

(21) Appl. No.: 09/919,262

(22) Filed: Jul. 30, 2001

(65) Prior Publication Data

US 2001/0047160 A1 Nov. 29, 2001

Related U.S. Application Data

(63) Continuation of application No. 09/215,473, filed on Dec. 18, 1998, now abandoned.

(51) Int. Cl.$^7$ ................................................. A61F 13/15
(52) U.S. Cl. ............................... 604/385.04; 604/385.24
(58) Field of Search ................................. 604/389, 391, 604/396, 385.03, 385.16, 385.22, 385.26, 385.27, 385.29

(56) References Cited

U.S. PATENT DOCUMENTS

| | | | | |
|---|---|---|---|---|
| 3,860,003 A | * | 1/1975 | Buell | 604/385.25 |
| 4,081,301 A | * | 3/1978 | Buell | 156/164 |
| 4,552,795 A | * | 11/1985 | Hansen et al. | 428/110 |
| 4,636,207 A | * | 1/1987 | Buell | 604/370 |
| 4,781,966 A | * | 11/1988 | Taylor | 428/152 |
| 4,857,067 A | * | 8/1989 | Wood et al. | 604/389 |
| 4,891,258 A | * | 1/1990 | Fahrenkrug | 428/138 |
| 5,236,430 A | * | 8/1993 | Bridges | 604/396 |
| 5,246,433 A | * | 9/1993 | Hasse et al. | 604/396 |
| 5,464,401 A | * | 11/1995 | Hasse et al. | 604/385.25 |
| 5,618,280 A | * | 4/1997 | Glackin et al. | 604/385.08 |
| 5,624,420 A | * | 4/1997 | Bridges et al. | 604/365 |
| 5,807,368 A | * | 9/1998 | Helmer | 604/373 |
| 5,843,068 A | * | 12/1998 | Allen et al. | 604/385.22 |
| 5,899,896 A | * | 5/1999 | Suprise et al. | 604/391 |

* cited by examiner

*Primary Examiner*—Weilun Lo
*Assistant Examiner*—Michael G. Bogart
(74) *Attorney, Agent, or Firm*—Alberto Q. Amatong, Jr.; The Morris Law Firm, P.C.

(57) ABSTRACT

A disposable absorbent garment includes a topsheet, a backsheet, and an absorbent core disposed between the topsheet and the backsheet. The topsheet, backsheet and absorbent core are assembled together to form a layered assembly including a front region, a back region, and a crotch region disposed between the front region and the back region. The layered assembly has a longitudinal plane that extends substantially centrally through the front, back and crotch regions. Each of the front and back regions further includes a pair of ear portions extending in substantially opposite lateral directions with respect to the longitudinal plane. Further, each of the ear portions includes a layered section of a material layer and a stretchable member extendible between a contracted configuration and an extended configuration. The material layer is secured to the stretchable member when the stretchable member is disposed in an extended configuration and the outside surface of the material layer is disposed in a substantially planar configuration. In this way, the material layer is, thereafter, extendible with the stretchable member from a contracted configuration to an extended configuration wherein its outer surface is returned to its substantially planar configuration.

29 Claims, 3 Drawing Sheets

DISPOSABLE ABSORBENT GARMENT HAVING STRETCHABLE SIDE WAIST REGIONS

CROSS REFERENCE TO RELATED APPLICATIONS

This application is a continuation of application Ser. No. 09/215,473, filed Dec. 18, 1998 now abandoned.

BACKGROUND OF THE INVENTION

The present invention relates generally to disposable absorbent garments and, more particularly, to a disposable absorbent garment having a stretchable ear portion and a method for making such a disposable absorbent garment.

Disposable absorbent garments contemplated by the invention include disposable diapers, disposable pull-on garments, and the like. These garments are worn about the lower torso or waist of the user so as to receive and contain urine and other bodily wastes. Disposable diapers are particularly intended for use on infants who depend on a caretaker to fit the diaper. Typically, the infant is laid down while the caretaker places the garment around the waist region of the infant and then secures two ends on each side of the diaper together.

Disposable pull-on garments include training pants, pull-on diapers, disposable underwear, and adult incontinence garments. It is generally expected that the user of any one of these garments will be able to put on and take off the garment on his\her own. As for training pants, these garments are intended for use on a young child just before or about the time the child is ready to graduate from diapers to regular underpants (i.e., during toilet training). Training pants (and other disposable pull-on pants) have closed sides such that the user or care giver raises the garment about the user's legs to put it on and slips the garment downward about the user's legs to take it off. Thus, training pants (and other pull-on pants) are designed to be put on and taken off in the same manner by which regular underpants are put on and taken off. This feature is particularly advantageous in toilet training because it provides an early introduction to underpants and, more specifically, trains the child to wear regular underpants. Similarly, it is advantageous that the training pants fit and look very much like regular underpants so that the child is comfortable in making the transition from training pants to regular underpants.

The principal elements that typically makeup the disposable absorbent garments described above are a liquid-permeable inner layer, a liquid-impermeable outer layer and an absorbent core sandwiched between the inner and outer layers. Elastic members may also be incorporated into different parts of the garments. For example, elastic members may be positioned longitudinally along the diaper, generally outboard of the absorbent core to effect a seal around the buttocks, legs or both of the user. In addition, several elastic members (e.g., in the form of elongated elastic threads) may be positioned laterally throughout the waist region (including the side waist regions) of a disposable absorbent garment to allow the garment to stretch when it is put on and then during wear. In this way, the garment can stretch to accommodate variations in waist size and leg size of the user, while fitting snugly about the waist and legs and without sagging. One drawback, however, is that the elastic strands are visible on the outer surfaces of the garment and can interfere to some extent with decorative or instructional printing displayed on the outer surfaces of the garment.

It is also known to provide disposable garments with separate side waist regions in the form of elastic side panels such as those disclosed in U.S. Pat. No. 4,938,753. The elastic side panels described therein have side edges which are attached to the outer edges of a central absorbent core assembly. The elastic side panels may be made from various elastomeric materials or combinations thereof and provide a more uniform fit generally more snug than side waist regions having elongated elastic strands. Moreover, the elastic side panels provide outer surfaces which are more uniform than the outer surfaces on side waist regions having elongated elastic strands. However, the elastomeric material for the side panel does not typically provide for a smooth, even outer surface when the side panels are in either the relaxed state or the stretched state. Accordingly, the side panels are not particularly conducive to having decorative or instructional printing displayed thereon.

Alternatively, it is known to provide a unitary pair of training pants with elasticized ear flaps such as those disclosed in U.S. Pat. No. 5,246,433. The elasticized ear flaps are formed by sandwiching a relaxed elastomeric element between two material layers of the ear flaps, and adhesively attaching the material layers to the relaxed elastomeric element to form an elastic laminate. The design also calls for mechanically stretching the elastic laminate such that the material layers permanently deform. Although the side waist region according to this design generally provides a more uniform fit than a side waist region having elongated elastic strands, the outside surfaces of the side waist region are not conducive to having decorative or instructional print displayed thereon because the mechanically stretched material layers are uneven and cannot fully return to their original undistorted configuration.

SUMMARY OF THE INVENTION

It is, therefore, a principal object of the present invention to provide a disposable absorbent garment that is stretchable or extendible to fit snugly around the waist region of the user, is comfortable to wear and is conducive to having decorative or instructional printing displayed thereon. More particularly, the disposable absorbent garment should have side waist regions or ear regions that specifically include these attributes.

It is another feature and object of the invention to provide a disposable absorbent garment in the form of a training pant or an adult incontinence garment that fits and looks very much like regular underpants.

It is yet another feature and object of the present invention is to provide a disposable absorbent garment in the form of a diaper that has extendible or elasticated ear portions which provide adjustable and comfortable fit.

It is yet another feature and object of the invention to provide a disposable absorbent garment that can accommodate a wide range of user waist and leg sizes.

It is yet another feature and object of the invention to provide a disposable absorbent garment that is aesthetically pleasing.

It is yet another feature and object of the invention to provide a disposable absorbent garment that fits snugly and minimizes sagging.

It is yet another feature and object of the invention to provide a method of manufacturing a disposable absorbent garment that promotes efficiency and product quality.

Thus, in accordance with one aspect of the present invention, there is provided a disposable absorbent garment that includes a first material layer on the inside of the garment (or top sheet), a second material layer on the outside of the garment (or backsheet), and an absorbent core disposed between the inner sheet and the outer sheet. These components are assembled together to form a layered assembly or composite web structure having a front region, a back region, and a crotch region extending between the front region and the back region. The layered assembly is also characterized by a longitudinal plane that extends substantially centrally through each of the front region, back region, and crotch region. Further, each of the front and back regions includes at least a pair of ear portions which extend in substantially opposite lateral directions with respect to the longitudinal plane. At least one, but preferably all, of the ear portions includes a layered section including at least one, but preferably two (e.g., an ear inner layer and an ear outer layer), outer material layer and a stretchable member (e.g., an elastic film or heat-activated film) extendible between a contracted configuration and an extended configuration. The outer material layer is secured to the stretchable member when the stretchable member is disposed in an extended configuration such that the outer material layer is subsequently contractible then extendible with the stretchable member.

In another aspect of the invention, the stretchable member is secured to the outer material layer such that the outer material layer is extendible with the stretchable member from a contracted configuration to an extended configuration. In its extended configuration, the outer material layer provides an outside surface that is disposed in a substantially planar configuration.

In accordance with another aspect of the present invention, there is provided a method of making a stretchable or elasticated ear portion in a disposable absorbent garment or alternatively, in a composite web structure of the garment. Such a web structure may be subsequently folded, cut, trimmed, or otherwise treated to form a finished disposable absorbent garment ready for packaging or wear. This method includes the initial steps of providing the following: a first layer (e.g., a topsheet) having front and back longitudinal ends and a pair of opposing lateral edges; a second layer (e.g., a backsheet) having front and back longitudinal ends and a pair of opposing lateral edges; an absorbent core; and at least one stretchable member (e.g., an elastic member). The stretchable member is positioned adjacent a first section of the first layer, the first section being located proximate one of the lateral edges and one of the longitudinal ends of the first layer and the second layer (i.e., an ear region). This first section is then secured to the stretchable member such that the first section is subsequently extendible with the stretchable member.

Then, the first layer, the second layer and the absorbent core are secured or otherwise assembled together to form a web structure having a central longitudinal plane and including a front region, a back region and a crotch region. The front region includes the front longitudinal ends (of the first and second layers) and a pair of ear portions extending in substantially opposite lateral directions with respect to the longitudinal plane. Similarly, the back region includes the back longitudinal ends (of the first and second layers) and a pair of ear portions that extend in substantially opposite lateral directions with respect to the longitudinal plane. As a further result, the first section and the stretchable member are included in one of the ear portions to form a stretchable ear portion in the web structure.

The disposable absorbent garment according to the invention (including disposable diapers, training pants, adult incontinence garments and other pull-on garments) has a side waist region that displays a smooth, substantially planar outer surface when the garment is worn and the side waist region is stretched or extended. More particularly, the garment has an extendible or elasticated side waist region formed by joining a pair of extendible or elasticated ear portions which can extend from a wrinkled or slacked configuration to an extended condition wherein it displays a smooth, substantially planar outer surface. To form the ear portion, an inside surface of the outer and\or inner layer of the ear portion is first extended (but not necessarily stretched) until it displays a smooth, substantially planar outer surface. Then, the inside surface of the layer is secured to a corresponding surface of a stretchable member (e.g., an elastic member) that is maintained in an extended configuration. When the stretchable member is allowed to contract, the secured layer contracts also and displays an outer surface characterized by wrinkles and a series of undulations (e.g., exhibits gathers). However, when the stretchable member is subsequently extended (e.g., when the garment is put on by the user), the secured layer extends with the stretchable member to smooth out its outside surface. The secured layer may be extended with the stretchable member to the extent the outside surface is returned to its initial substantially planar configuration.

The side waist regions of the invention advantageously allows for an improved snug fit, yet comfortable, waist fit that can adjust dynamically to the wearer's waist expansion and contraction. Additionally, the side waist region's smooth appearance when extended provides for the inclusion of decorative and\or instructional printing on the outer surfaces of the ear portions which are legible (i.e., "unbroken"), aesthetically pleasing and practical. Moreover, the side waist regions can combine with the front and back waist regions to provide a substantially continuous smooth surface all around the garment whereon decorative or instructional printing may be displayed.

It should again be noted that the invention is adaptable to various types of disposable absorbent garments including, but not limited to, disposable diapers, training pants, adult incontinence garments and other pull-on garments.

These and other objects, features and advantages of the present invention will become apparent to those skilled in the art from the following detailed description and the drawings.

DETAILED DESCRIPTION OF THE DRAWINGS

Figures 1, 2:
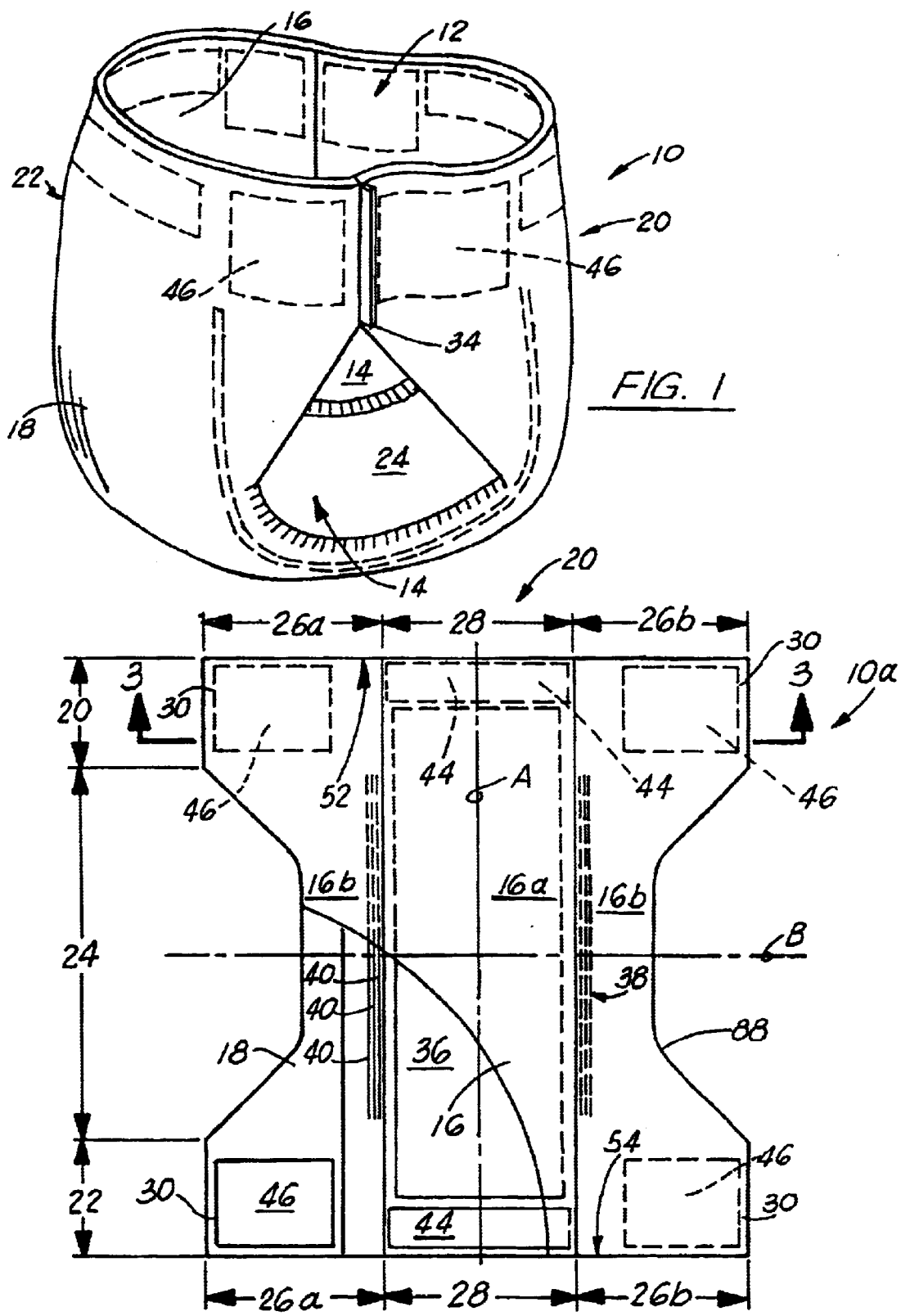
FIG. 1 is a perspective view of a disposable absorbent garment according to one embodiment of the present invention shown as it would appear worn around the waist region of a user.
FIG. 2 is a top plan view of the garment in a flat and extended condition with portions cut away to reveal an underlying structure.

FIG. 1 depicts a disposable absorbent garment 10 embodying the invention and in the form of a training pant or adult incontinence garment. The garment 10 is formed with a waist opening 12 and two leg openings 14, and is shown as it would appear worn about the lower torso or waist region of a user. FIG. 2 depicts a composite web structure 10a of the garment 10 in a flat and unfolded configuration, which it assumes during one point in the manufacturing process when it is stretched in both the lateral and longitudinal directions. As will be further explained below, the web structure 10a may be subsequently trimmed, folded, sealed, welded and\or otherwise manipulated to form a disposable garment 10 in final form and for packaging. In particular, the view of FIG. 2 is provided to reveal with clarity most of the major elements of the disposable absorbent garment 10 and\or web structure 10a according to the present invention.

It should first be noted that, upon review of the detailed description and the drawings provided herein, it will become apparent to one of ordinary skill in the art that the present invention is also applicable to other disposable absorbent articles and, more particularly, to disposable absorbent garments other than training pants and adult incontinence garments. Accordingly, the present invention is not intended to be limited to the structures and processes specifically described and illustrated herein.

The garment 10 features a layered assembly or composite web structure 10a that includes a liquid-permeable inner layer or topsheet 16, a liquid-impermeable outer layer or backsheet 18, and an absorbent core 36 disposed therebetween. Now referring specifically to the view of FIG. 2, the web structure 10a may be described further with reference to a longitudinally extending central axis A and a laterally or transversely extending central axis B. Along the longitudinal axis A, the garment 10 features a front waist region 20 having a front edge or front longitudinal end 52, a back waist region 22 having a back edge or back longitudinal end 54, and a crotch region 24 extending between the front waist region 20 and the back waist region 22. Along the lateral direction and with specific reference to the view of FIG. 2, the front waist region 20 includes a left ear region 26a, a central body region 28, and a right ear region 26b. Similarly, the back waist region 22 includes a left ear region 26a, a central body region 28, and a right ear region 26b. The web structure 10a also has a longitudinal side edge 88 that extends between each pair of ear regions 26a, 26b and spaced on each side of the absorbent core 36.

Further, each of the ear regions 26 has a side edge area 30. During a latter stage in the manufacturing process, ear regions 26a are joined together by mating their respective side edges 30, to form a side seam 34 (see FIG. 1). The ear regions 26b are similarly joined. The ear regions 26a and 26b may be joined together according to many different procedures well known to those skilled in the art. For example, the ear regions 26a, 26b may be ultrasonically welded or adhesively joined, to mention only a couple of approaches. Upon completion of both side seams 34, waist opening 12 and leg openings 14 are formed in the disposable absorbent garment 10.

Referring to FIG. 1, when the garment 10 is properly worn about the waist region of the user, the topsheet 16 generally contacts the buttocks of the user while the backsheet 18 faces outwardly from the body of the user. Further, the front waist region 20 of the garment 10 is situated at the front waist area of the user and the back waist region 22 is situated at the back waist area of the user, while the crotch region 24 is situated between the legs of the user and at the crotch area. As for the ear regions 26, each pair of adjoined ear regions 26a, 26b is designed to fit snugly about the side waist region of the user with the side seams 34 positioned preferably in a substantially vertical orientation.

The backsheet 18 may be constructed from a number of different suitable materials and, preferably, will have a breathable or vapor-permeable attribute (distinguishing it from liquid-permeable) so that air can pass therethrough. In one embodiment, the backsheet 18 is constructed from a polyolefin film. Alternatively, the backsheet 18 may be formed from a combination of a liquid-permeable, nonwoven material and a film barrier that is laminated on the nonwoven material. The film barrier may or may not be vapor-permeable. Further, the film barrier may be applied as a mask in a central area of the web structure 10a that has an overall width less than the width of the other backsheet materials but covers the absorbent core 36. One suitable construction for the backsheet 18 includes an outer layer of spunbond polypropylene fiber with a basis weight of about 15 gsm (available from BBA Nonwovens, of Simpsonville, S.C.) and a polyethylene film of about 0.5 mil (0.0005") thickness adhesively laminated to the outer layer. Such a polyethylene film is available from, and manufactured by, Exxon Chemical USA, of Houston, Tex. The film may be laminated using adhesive available from National Starch & Chemical Company of Bridgewater, N.J. Yet another suitable construction for the backsheet 18 includes a web of spunbond or SMS (spunbond\meltblown\spunbond) nonwoven material and breathable or non-breathable films of 0.5 mils to 2.0 mils in thickness.

For purposes of description, the term "backsheet" or "outer layer," as used herein, may refer to any sheet, layer or composite that covers at least the core 36, but preferably extends laterally beyond the core 36 toward the side edges 30 and longitudinal side edges 88 of the garment 10 or web structure 10a. Further, the term "backsheet" or "outer layer," as used herein, may refer to any assembly, unitary or integrally, of sheets, layers, or composites applied at least over the core 36, and any part, portion, region or section thereof.

In the embodiment depicted in the drawings, the backsheet 18 is a single sheet material that provides the outer layer of each of the ear regions 26 as well as the outer layer of the rest of the front and back regions 20, 22 and the crotch region 24. Thus, the outer layer of each ear region 26 may be referred to as being unitary with, and forming a lateral extension of, the rest of the backsheet material. In alternative embodiments, however, the backsheet 26 may include a central section and a pair of left and right side panels or sheets which are distinct from the central section. Each of the side panels is joined to and, thereby, integrated with the central section. The left side panel extends between each of the left ear regions 26a and provides an outer layer common to both ear regions 26a. Similarly, the right side panel extends between each of the right ear regions 26b and provides an outer layer common to both right ear regions 26b. In yet another embodiment, the backsheet 18 includes, in addition to a central section, four separate side panels: a front right ear panel, a back right ear panel, a front left panel, and a back left panel. Each of the panels forms an outer layer of an ear region 26 and is joined to, and integrated with, the central section of the backsheet 18.

Figure 3:
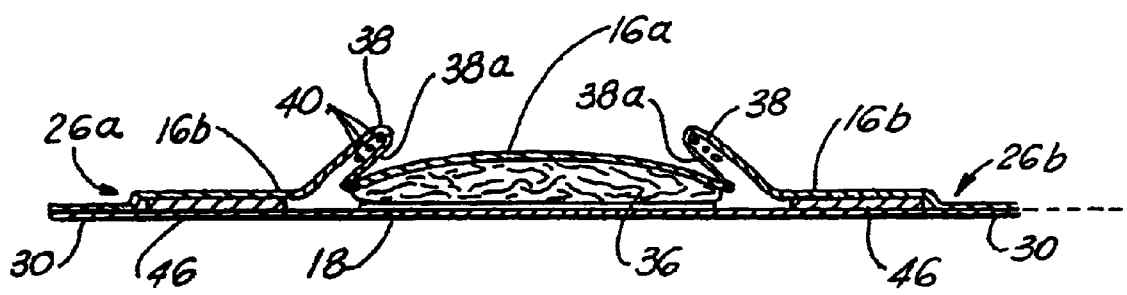
FIG. 3 is a cross sectional view of the garment taken along line 3—3 in FIG. 2.

The absorbent core 36 is generally elongated and rectangular in shape. As best shown in FIGS. 2 and 3, the core 36 is generally centered about the longitudinal axis A and lateral axis B of the garment 10, and firmly secured between the topsheet 16 and backsheet 18. The core 36 is preferably made of an absorbent composition adapted to absorb bodily liquids received through the topsheet 16. Typically, the absorbent composition includes a fluffed wood pulp component for wicking and structural integrity and a high absorbency material (or super absorbent) for containing liquids. However, the garment 10, according to the present invention, is equally adapted to utilize absorbent cores of varying shapes and compositions, as well as other types of cores known in the art.

The topsheet 16 may be constructed from a wide range of suitable materials including nonwoven webs of natural fibers (e.g., wood or cotton) or synthetic fibers (e.g., polypropylene or polyester), a combination of such webs or fibers, or apertured film. One suitable topsheet material is a 15 gsm spunbond polypropylene from Avgol Nonwoven Fabrics of Holon, Israel. In addition, the topsheet 16 may be treated with a surfactant to facilitate liquid transfer, especially at a central zone of the topsheet 16 over the core 36, and an inner surface of the topsheet 16 may be treated with a chemical to increase the surface tension of liquid passing through the material.

For purposes of description, the term "topsheet" or "inner layer," as used herein, may refer to any sheet, layer or composite that covers at least the core 36, but preferably extends beyond the core 36 toward the side edges 30 and longitudinal side edges 88 of the garment 10 or web structure 10a. Further, the term "topsheet" or "inner layer," as used herein, may refer to any assembly, unitary or integrally, of sheets, layers, or composites applied at least over the core 36, and any part, portion, region or section thereof.

In one embodiment, the topsheet 16 is formed from a single piece or sheet of material that covers substantially all of the entire area of the garment 10, including substantially all of the front waist region 20, back waist region 22, and crotch region 24. In such an embodiment, the inner layer of the ear regions 26 are formed from the same single topsheet material, and are referred to as being unitary with and forming lateral extensions of the topsheet material. Alternatively, the topsheet 16 may be formed from multiple materials which vary across the width of the topsheet 16, as illustrated in the web structure 10a depicted in FIGS. 2 and 3. Such a multiple-piece design allows for the creation of preferred properties in different zones of the topsheet 16. Referring to FIGS. 2 and 3, for example, the topsheet 16 is formed from a three-piece sheet material including a hydrophilic material to form a center section 16a above the absorbent core 36 and a hydrophobic material to form a pair of barrier cuffs with lateral side sections 16b distinct from the center section 16a. The lateral side sections 16b are joined to and integrated with the center section 16a of the topsheet 16 via adhesive means, welding means and the like. The lateral side sections 16b also provide outer layers common to the left and right ear regions 26a, 26 respectively In some instances, the multiple-piece construction of the topsheet 16 facilitates the manufacturing process for the garment 10 because certain regions (e.g., the ear regions 26) can remain uncovered (by the topsheet 16) even after center section 16a is applied over the core 36. In this way, the uncovered regions may be treated or finished at a later stage in the manufacturing process.

Referring again to FIG. 2, the web structure 10a of garment 10 may also include a pair of longitudinally extending barrier cuffs 38 which are formed along lateral side sections 16b. An inner portion 38a of the barrier cuffs 38 is glued to, or otherwise engaged with, an outer edge of the central section 16a of the topsheet 16. The barrier cuffs 38 are preferably positioned on either side of and spaced from longitudinal axis A and outboard of the core 36, and extend upwardly from the topsheet 16 (i.e., toward the user). The longitudinal ends of the cuffs 38 may be attached, for example, to the topsheet 16 in the front and rear waist regions 20, 22. Preferably, the ends of the barrier cuffs 38 are tacked down inwardly and attached, for example, by adhesive, to the web structure 10a. Such a construction biases the cuff 38 inwardly and is generally considered to cause the cuff 38 to exhibit improved leakage prevention properties.

Preferably, the barrier cuffs 38 are equipped with elastic members 40 which extend along a substantial length of the barrier cuffs 38. In a common application, the elastic members 40 are placed within or underneath the barrier cuffs 38 while in a stretched condition and then glued to the cuff at least at their ends. When released or otherwise allowed to relax, the elastic members 40 retract inwardly. When the garment 10 is worn, the elastic members 40 function to contract the barrier cuffs 38 about the buttocks of the user in a manner which effects a seal between the garment 10 and the buttocks.

The barrier cuffs 38 may also be formed by a number of alternative methods known in the art. One method involves gluing a separately constructed barrier cuff 38 to the top surface of the web structure 10a. Another method involves forming the barrier cuff 38 from the topsheet 16 or backsheet 18. Yet another method involves creating and folding noodle cuffs as disclosed in U.S. Pat. No. 5,536,350, which is hereby incorporated by reference. The present invention is equally adapted to employing any of these barrier cuff constructions and other cuff constructions known in the art.

In an alternative embodiment of the invention, a longitudinally stretchable gasketing cuff is positioned proximately each longitudinal side edge 88. When the garment 10 is properly worn by the user, each gasketing cuff encircles a leg of the user and effects a seal thereon to prevent leakage. Generally, the gasketing cuff is formed with elastic members which are typically applied in the stretched or extended condition and are placed between the topsheet 16 and backsheet 18. The elastic members are glued or otherwise secured to one or both of the topsheet 16 or backsheet 18, or other material layer of the web structure 10a. Upon release from its stretched condition, the elastic members retract with the attached material layer and form gathered leg regions.

The present invention is adapted to use other gasketing cuff constructions known in the art. Moreover, the present invention may utilize gasketing cuffs in combination with barrier cuffs 39 as described above or, alternatively, alone without barrier cuffs.

Still referring to FIG. 2, the web structure 10a may be further equipped with an elastic waist band 44 that is inserted between the topsheet 16 and backsheet 18 and adjacent the central body regions 28 of each of the front waist region 20 and back waist region 22. In other forms of the invention, the waist band 44 may be omitted or may be extended substantially continuously along the top end of the front waist region 20 and back waist region 22, thereby encircling or partially encircling the waist of the user when the garment 10 is worn. The waist band 44 is preferably made of an open cell urethane foam available from General Foam, of Paramus, N.J.

Now referring to both FIGS. 2 and 3, the web structure 10a of disposable absorbent garment 10, according to the invention, is further equipped with a stretchable member 46 (e.g., an elastic member) substantially incorporated with, and made a part of, one or more of the ear regions 26. As best shown in FIG. 3, the stretchable member 46 is preferably interposed between the topsheet 16 and backsheet 18 in the ear regions 26. The stretchable member 46 extends longitudinally from nearly adjacent a longitudinal end 52 towards the crotch portion 24 (i.e., about 5–6" long) and laterally from substantially proximate the central body portion 28 toward the side edge area 30. However, the stretchable member 46 should be spaced sufficiently inwardly from the side edge area 30 so as not to be affected by or to affect the attachment of the side edges 30 to one another to form the garment 10. Furthermore, the present invention is not limited to specifically sized or positioned stretchable members 46. Instead, the stretchable member 46 may assume a variety of shapes and sizes and may be positioned at various locations within the ear regions 26 as long as the stretchable member 46 provides the ear regions 26 with sufficient extensibility to accomplish joinder of the ear regions 26 to form a waist region.

When the ear regions 26 are joined by the welding process, there is formed an absorbent garment 10 having stretchable side waist regions formed by the pairs of ear regions 26a, 26b. The stretchable member 46 is designed and is positioned within the ear regions 26 to facilitate stretching of the ear regions 26 in the lateral direction. The garment 10, therefore, can extend around and contract toward the side waist region of the user, and effect a snug fit. In one alternative embodiment of the invention, a substantially continuous elongated stretchable member 46 is positioned along both the front waist region 22 and back waist region 20, thereby acting as a nearly continuous belt around the user. The continuity of the belt is interrupted only by the side seams 34. In such an embodiment of the invention, the foam waist band 44 is preferably eliminated.

In a unique aspect of the invention, the ear regions 26 are attached to the stretchable member 46 when the stretchable member 26 is in a stretched or extended configuration. In forming an ear region 26, the stretchable member 46 is first extended or otherwise stretched laterally and then the inside surface of the topsheet material and\or backsheet material at the ear region 26 is\are secured or otherwise attached to a corresponding surface of the stretchable member 46 by conventional adhesive or mechanical means. It is important to extend the sheet material(s) to an extent where it displays a smooth, flat outer surface, but not necessarily to the extent where the material stretches and\or deforms. When the stretchable number 46 is then allowed to contract or relax, the topsheet material and\or backsheet material contracts with it.

Figure 4:
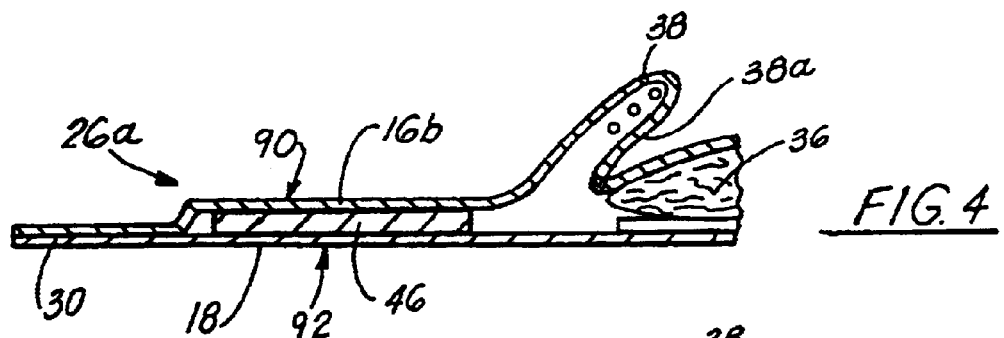
FIG. 4 is a cross sectional view of an ear region of the garment disposed in an extended configuration.
Figure 5:
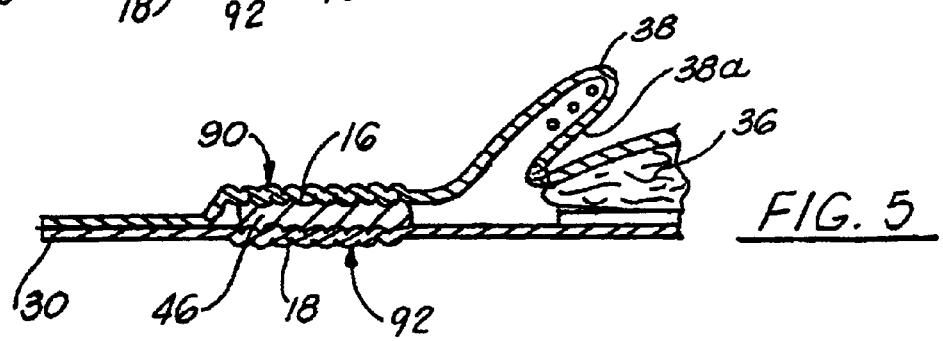
FIG. 5 is a cross sectional view of the ear region in FIG. 4 disposed in a contracted condition.

To illustrate, FIG. 4 depicts the ear region 26 having an outer layer provided by the singlesheet backsheet material and formed unitary with the rest of the backsheet 18, and an inner layer provided by the barrier cuff lateral section 16b of the top sheet 16. The ear region 26 is shown immediately after a section of both the barrier cuff 16b and the backsheet 18 are attached to the stretchable member 46 (and also when the garment 10 is worn by the user). In this view, the stretchable member 46 is maintained in the stretched or extended configuration, and the top cuff 16b and backsheet 18 each display flat, smooth outer surfaces 90, 92 respectively. FIG. 5 depicts the ear region 26 after the stretchable member 46 is released and allowed to contract laterally to a relaxed, contracted or unstretched configuration. Preferably, the stretchable member 46 contracts from an initial width of about 4½" to 5½ to a relaxed or contracted width of about 2" to 3". The layered composite that is formed by the barrier cuff lateral sections 16b, backsheet 18 and stretchable member 46 is moved inwardly toward the barrier cuff 38 and, as a result, the lateral width of the garment 10 is reduced (e.g., from about 15" to 16" across to about 11" to 12" across). Moreover, the outer surface 90 of the lateral section 16b and the outer surface 92 of the backsheet 18 are slacked and form wrinkles and undulations on both sides of the stretchable member 46 (i.e., exhibit gathers).

Figure 6:
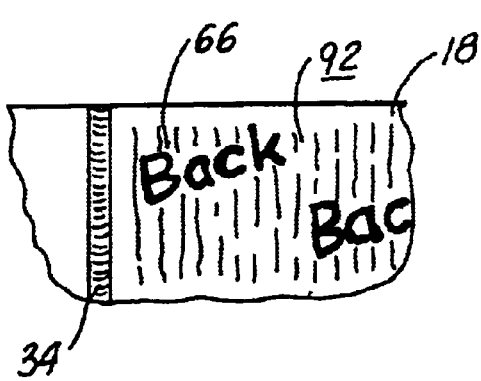
FIG. 6 is a bottom plan view of the ear region of the garment in FIG. 4 disposed in the extended configuration.
Figure 7:
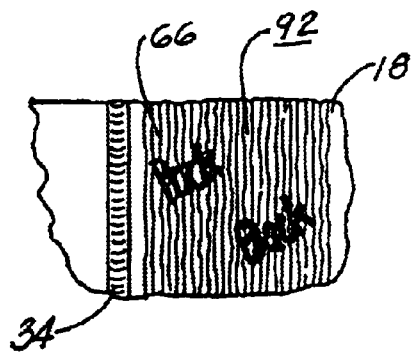
FIG. 7 is a bottom plan view of the ear region of the garment in FIG. 4 disposed in the contracted condition.

To further illustrate, the bottom plan view of FIG. 6 is provided to show the condition of the backsheet 18 when the stretchable member 46 (and the stretchable ear portion 26) is disposed in an extended or stretched configuration (e.g., when the garment 10 is worn by the user). In the extended configuration, the backsheet 18 displays a smooth, continuous outer surface 92 that is particularly conducive to having decorative or instructional printing 66 displayed thereon. Thus, when the garment 10 is worn around the waist of the user, the front and back waist regions 20, 22 together display a continuous, smooth outer surface substantially all around the waist of the user except where it is interrupted by the side seams 34. Conversely, FIG. 7 is a bottom plan view showing the condition of the backsheet 18 when the stretchable member 46 is disposed in the contracted or unstretched condition (e.g., when the garment 10 is not being worn by the user). In this view, the outer surface 82 of the backsheet 18 at the ear region 26 is characterized by wrinkles and a series of undulations (i.e., exhibits gathers).

It should be further noted that neither the barrier cuff lateral section 16b nor the backsheet 18 is permanently elongated during the forming of the composite layer, or during normal subsequent wear. In other words, the topsheet 16 and backsheet 18 are not stretched beyond its elastic region, and in some processes are merely extended to smooth out the outer surface, but not stretched beyond that point. In summary, the topsheet 16 (i.e., top cuff 16b) and backsheet 18 are merely stretched or extended to form flat, smooth surfaces 90, 92 during manufacturing and when the garment 10 is worn about the user, but retracts to a wrinkled, contracted state when the garment 10 is otherwise not worn.

The stretchable member 46 may be formed from an elastic material, such as the material typically used for the elastic waistband 44, or any other material with the appropriate stretch and return properties. The stretchable member 46 may be also formed from a heat-activated elastomeric material or elastomer that is elasticized upon initial application of a pre-determined amount of heat. The heat-activated elastic also contracts from an extended configuration to a contracted condition upon the initial application of heat in the vicinity of the stretchable member 46. In a process which makes use of the heat-activated elastomer, sections of the topsheet 16 and backsheet 18 are fastened to opposite surfaces of a stretchable member 46 incorporating the heat-activated elastomer and then contract with the stretchable member 46 upon the initial application of heat to the elastic. The stretchable member 44 incorporating the heat-activated elastomer may stretch or extend laterally when the garment 10 is worn around the waist of the user and then retract to its contracted, relaxed or unstretched configuration when the garment 10 is not being worn. Further, the materials of the barrier cuff lateral section 16b and the backsheet 18 can extend laterally with the stretchable member 46 to display flat, smooth outer surfaces 90, 92 at the ear regions 26 and then contract with the stretchable member to display outer surfaces 90, 92 characterized by wrinkles and a series of undulations, and exhibiting gathers.

Figure 9:
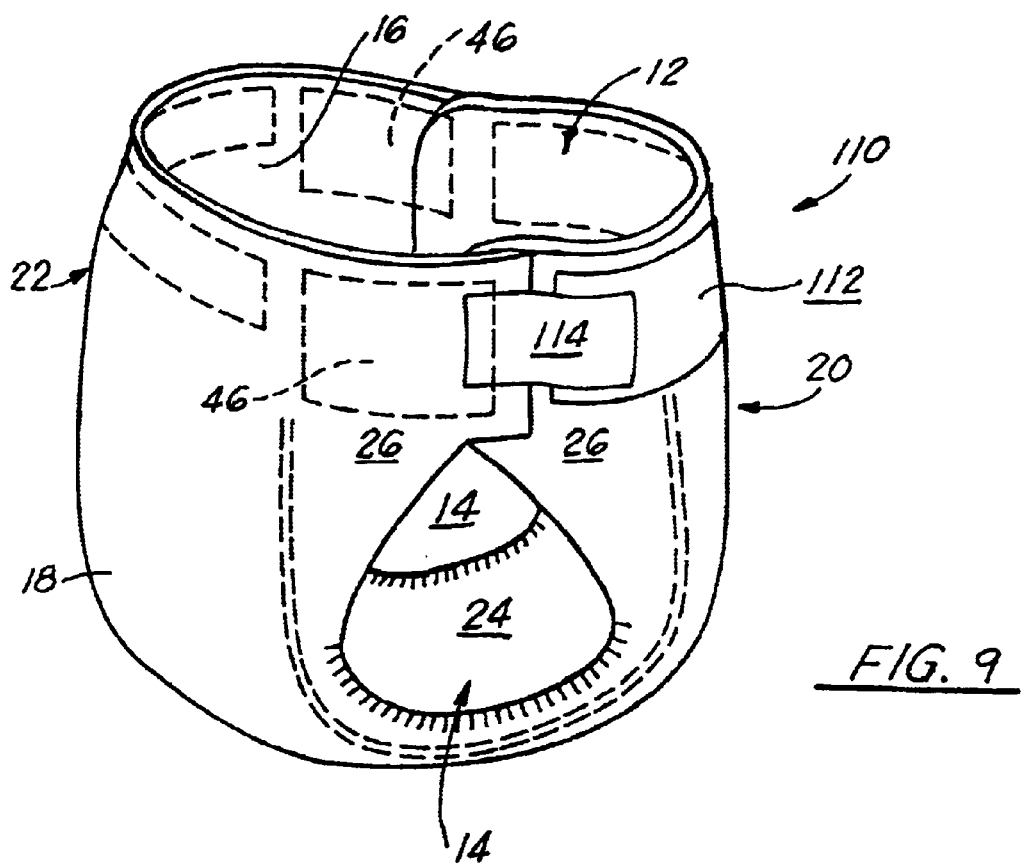
FIG. 9 is a perspective view of a disposable absorbent garment according to another embodiment of the present invention shown as it would appear worn around the waist region of a user.

FIG. 9 depicts an alternative embodiment of the disposable absorbent garment according to the invention, wherein like elements are referred to using like reference numerals. The disposable garment is in the form of a disposable diaper 110, and is shown as it would appear worn about the lower torso or waist region of the user. The construction of diaper 110 is similar in many respects to the disposable garment 10 illustrated in FIGS. 1 through 9, including the fact that it incorporates a stretchable member 46 into each of its four ear regions 26 in the same manner previously described. The diaper 110 is further equipped with fastening means in the form of a strip of frontal tape 112 attached to the backsheet 18 at the front region 20 and a pair of tape tabs 114. Each of the tape tabs 114 is attached to the backsheet 18 at an ear region 26. As is conventional, the tape tabs 114 are releasably fastenable at any point along the strip of frontal tape 114 to secure the diaper 110 around the waist region of the user. The combination of the frontal tape-tape tabs fastening means with the stretchable ear regions 26 of the present invention provides an improved means for adjustably fitting and securing a disposable diaper (and similar garments) around the waist of the user.

It should be understood that the present invention is adapted to incorporate a system of frontal tape 112 and associated tape tabs 114 according to any one of several designs known in the art. Further, the present invention is adapted to incorporate several other types of fastening means, including a hook and loop system.

Figure 8:
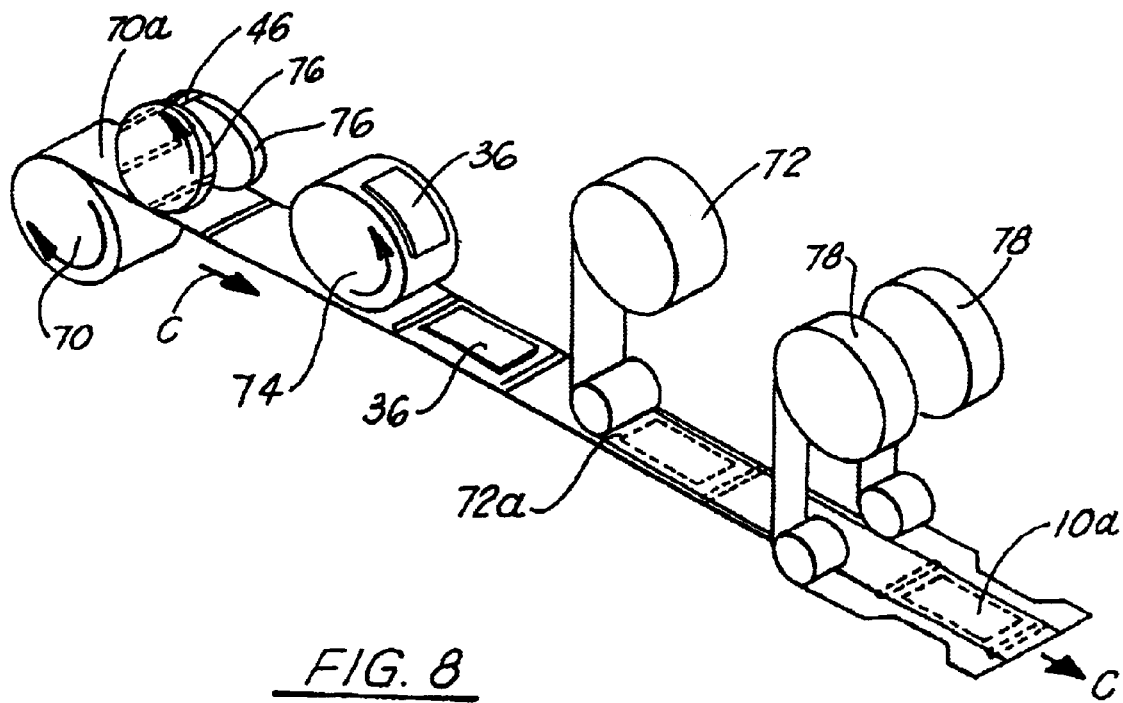
FIG. 8 is a diagrammatic view of a system for assembling a composite web structure used to form the garment.

One suitable apparatus or system for manufacturing the garment 10 and, more specifically, for providing a stretchable ear portion 26 in a web structure 10*a*, is illustrated in the diagram of FIG. 8. It should first be noted that the schematic of FIG. 8 illustrates in simplified form only one of several systems that is suitable for practicing the present invention. Other variations of the illustrated system and other known systems may be successfully employed to form the garment 10 of the invention and will be apparent to one skilled in the art. One such apparatus is described in U.S. Pat. No. 5,308,345 (hereby incorporated by reference) assigned to Tharpe.

In one suitable method of manufacturing, a supply roll 70 feeds a continuous supply of sheet material, such as backsheet material 70*a*, to a pair of rotatable conveyor track or wheels 76 which deposits thereon stretchable members 46. The stretchable member 46, which may be in the form of either a film or a patch, is carried on the outer radial surfaces of the wheels 76 and are deposited on the backsheet material 70*a* in staggered fashion. The wheels 76 are gradually spaced further apart in the direction of stretchable member travel and have outer gripping surfaces (not shown) which are adapted to grip an end of the stretchable member 46. As the stretchable member 46 is carried forward by the conveyor wheels 76, it is gradually stretched in the lateral or cross-machine direction between the wheels 76 until it contacts the substantially flat sheet of backsheet material 70*a*. When the stretchable member 46 contacts the backsheet material 70*a*, the stretchable member 46 is disposed in the stretched condition and the backsheet material 70*a* is extended in both the lateral and longitudinal directions, such that its inside and outside surfaces are smooth and substantially planar. Glue or other adhesive may be applied on the backsheet material 70*a* and\or the stretchable member 46 prior to these two elements coming into pressurized contact.

As noted earlier, one or more stretchable members 46 may be applied at various locations on the backsheet 18 or topsheet 16. To accommodate such alternative designs, the speed of the wheels 76 may be adjusted relative to the supply speed of the backsheet 70*a*, the position of wheels 76 may be moved, and/or additional pairs of wheels 76 may be employed.

After the stretchable members 46 are applied on the backsheet material 70*a*, the backsheet material 70*a* is moved forward to a drum 74. The drum 74 deposits a series of absorbent cores 36 onto the backsheet material 70*a*, typically in position between pairs of stretchable members 46. Thereafter, a second supply roll 72 applies a continuous sheet 72*a* of center section 16*a* of the topsheet material over the backsheet material 70*a*, the absorbent cores 36 and stretchable member 46. This is immediately followed by a pair supply rolls 78 which are employed to deposit lateral sections 16*b* of the topsheet 16 and to form composite web structure 10*a*.

For clarity, application of waist elastic members, barrier cuffs, and leg cuffs to the web structure 10*a* are not shown or described. It should be understood, however, that the present invention is adapted to incorporating various constructions of these components and suitable methods of applying such constructions onto a composite web structure 10*a*.

After supply rolls 78, the continuous composite web structure 10*a* may be passed through a bonding station where the appropriate edges of the sheets of lateral sections 16*b*, center section 16*a*, and backsheet 18 are bonded together. Any suitable method of bonding, including ultrasonic, thermal, or adhesive bonding may be employed. Then, the composite web structure 10*a* is passed through a die cut station wherein the leg openings are cut out from each of the lateral sections 16*b* and the corresponding section of the backsheet 18. Then, the continuous composite web structure 10*a* is cut at a knife station to form individual web structures 10*a*. Each web structure 10*a* is subsequently folded about the lateral axis B by a fold bar to mate the pair of ear regions 26. The folded web structure 10*a* is then passed through a seam welding station where side edge areas 30 of the ear regions 26 are joined together—for example, by ultrasonic welding.

It should be noted that the web structure 10*a* and the components that make up the web structure are positioned in the in-line or machine direction C during the preferred manufacturing process (i.e., wherein the longitudinal axis A is coincidental with the direction of web travel). Applicant believes that positioning the web structure 10*a* in this manner furthers efficiency in the manufacturing process and promotes quality in the final product. In one aspect of the invention, the design of the web structure 10*a* and the garment 10, particularly the use of the stretchable member 46 instead of elongated elastics threads which are directed laterally across the width of the garment 10, allows for such an in-line process of manufacturing to be employed.

Although several embodiments of the present invention have been shown or described, alternate embodiments will be apparent to those skilled in the art and are within the scope of the present invention. Therefore, the invention is to be limited only by the claims.

What is claimed is:

1. A disposable absorbent garment, comprising:

a topsheet;

a backsheet; and an absorbent core disposed between said topsheet and said backsheet, said topsheet, said backsheet and said absorbent core being assembled together to form a layered assembly including a front region, a back region, and a crotch region disposed between said front region and said back region, said layered assembly having a longitudinal plane that extends substantially centrally through said, front, back and crotch regions;

wherein each of said front and back regions further includes at least a pair of ear portions extending in substantially opposite lateral directions with respect to said longitudinal plane, and wherein at least one of said ear portions includes a layered section comprising an outer material layer having an inside surface and an outside surface, said outside surface having a decorative or instructional display thereon and an elastic stretchable non-permanently elongated member extendible between a contracted configuration and an extended, non-permanently elongated configuration, said inside surface being secured to a corresponding surface of said stretchable member when said stretchable member is disposed in an extended configuration and said outside surface is disposed in a substantially planar configuration, wherein said display is observable thereon such that said outer material layer is subsequently contractible then extendible with said stretchable member and such that said outside surface is returnable to said substantially planar configuration without permanent elongation of said outer material layer and said stretchable non-permanently elongated member, wherein said display on said outside surface is unobscured and observable when said outside surface is disposed in said substantially planar configuration and said display is substantially less observable and less unobscured when said stretchable member is disposed in a contracted configuration.

2. The garment of claim 1, wherein said outside surface is returned to said substantially planar configuration when said stretchable member extends from a contracted configuration to an extended configuration.

3. The garment of claim 1, wherein said outer material layer is secured to said stretchable member such that said outer material layer exhibits gathers when said stretchable member is disposed in said contracted configuration.

4. The garment of claim 1, wherein said stretchable member includes a heat-activated elastomer that contracts from an initial extended configuration upon application of heat, and wherein said outer material layer is secured to said stretchable member when said heat-activated elastomer is disposed in said initial extended configuration.

5. The garment of claim 1, wherein said ear portions of said front region are joined to corresponding ear portions of said back region to form a waist opening and a pair of leg openings.

6. The garment of claim 1, wherein said stretchable member is an elongated member having a first end and a second end, said first end being disposed in an ear portion of said front region and said second end being disposed in an ear portion of said back region.

7. The garment of claim 1, wherein said stretchable member is an elongated stretchable member having a first end and a second end, said first end being disposed in said at least one ear portion and said second end being disposed in a second ear portion, wherein said at least one ear portion is disposed on one side of said longitudinal plane and said second ear portion is disposed on an opposite side of said longitudinal plane.

8. The disposable garment of claim 1, wherein said stretchable member is positioned within said ear portion such that said ear portion is stretchable in a direction substantially lateral with respect to said longitudinal plane.

9. The garment of claim 1, wherein said layered section further includes a second outer material layer secured to a surface of said stretchable member generally opposite to said corresponding surface of said stretchable member, and wherein said stretchable member is disposed between said first outer material layer and said second outer material layer, said first and second outer material layers being secured to said stretchable member when said stretchable member is disposed in said extended configuration such that said first and second outer material layers are subsequently contractible then extendible with said stretchable member.

10. The garment of claim 9, wherein said backsheet includes a backsheet central section and said topsheet includes a topsheet central section, and wherein said first outer material layer is formed unitary with said backsheet central section and said second outer material layer is formed unitary with said topsheet central section.

11. The garment of claim 9, wherein said first outer material layer is a portion of said backsheet, and wherein said topsheet includes a top sheet central section, said second outer material layer being a portion of said topsheet that is distinct from and joined integrally with said topsheet central section.

12. The garment of claim 1, wherein each of said other ear portions includes a layered section comprising an outer material layer, and a stretchable member extendible between a contracted configuration and an extended configuration, said outer material layer being secured to said stretchable member when said stretchable member is disposed in an extended configuration such that said outer material layer is subsequently contractible then extendible with said stretchable member.

13. A disposable absorbent garment comprising:

a layered core assembly including a topsheet, a backsheet, and an absorbent core positioned between said topsheet and said backsheet; and at least a pair of extendible ear assemblies positioned on laterally opposite sides of said layered assembly, each of said ear assemblies including an elastic stretchable non-permanently elongated member and an outer material layer joined to said elastic member, said outer material layer having an outside surface and an inside surface, said inside surface being secured to a corresponding surface of said elastic member when said elastic member is disposed in an extended configuration, said outside surface having a decorative or instructional display thereon, wherein said outer material layer exhibits gathers when said elastic member is disposed in a relaxed configuration, said elastic member being extendible between a contracted configuration and an extended, non-permanently elongated configuration, said inside surface being secured to a corresponding surface of said stretchable member when said stretchable member is disposed in an extended configuration and said outside surface is disposed in a substantially planar configuration, wherein said display is observable thereon such that said outer material layer is subsequently contractible then extendible with said stretchable member and such that said outside surface is returnable to said substantially planar configuration without permanent elongation of said outer material layer and said stretchable non-permanently elongated member, wherein said display on said outside surface is unobscured and observable when said outside surface is disposed in said substantially planar configuration and said display is substantially less observable and less unobscured when said stretchable member is disposed in a contracted configuration.

14. A method of making a stretchable ear portion in a composite web structure used for forming a disposable absorbent garment, said method comprising the steps of:

providing a first layer having a front longitudinal end, a back longitudinal end and a pair of opposing lateral edges therebetween;

providing a second layer having a front longitudinal end, a back longitudinal end, and a pair of opposing lateral edges therebetween;

providing an absorbent core;

providing a stretchable member contractible from a stretched configuration to a contracted configuration;

positioning said stretchable member adjacent a first section of said first layer, said first section being located proximate one of said lateral edges and one of said longitudinal ends of said first layer and having an inside surface and an outside surface generally opposite said inside surface, said outside surface having a decorative or instructional display printed thereon;

securing said inside surface to said surface of the stretchable member when said outside surface is disposed in a substantially planar configuration such that said display is observable thereon and said stretchable member is disposed in a stretched configuration, such that said first section is subsequently extendible with said stretchable member from a contracted configuration in which said display is substantially less observable and less unobscured to an extended configuration wherein said outer surface is returned unaltered to said substantially planar configuration, and securing said first layer, said second layer and said absorbent core together to form a web structure having a central longitudinal plane and including a front region that includes said front longitudinal ends and a pair of ear portions extending in substantially opposite lateral directions with respect to said longitudinal plane, a back region including said back longitudinal ends and a pair of ear portions extending in substantially opposite lateral directions with respect to said longitudinal plane, and a crotch region disposed between said front region and said back region, whereby said stretchable member and said first section are included in one of said ear portions to form a stretchable ear portion.

15. The method of claim 14, wherein said step of providing a stretchable member includes providing a stretchable member including a heat-activated elastomer that contracts from an initial extended configuration upon application of heat, said method further comprising the step of:

applying heat in a vicinity of said stretchable material, alter said step of securing first section to said stretchable member, to contract said stretchable member and said first section to a contracted configuration and to activate the elasticity of said elastomer.

16. The method of claim 14, wherein said step of positioning said stretchable member includes positioning said stretchable member adjacent a second section of said second layer, wherein said second section is located proximate one of said lateral edges and one of said longitudinal ends of said second layer, said method further comprising the step of securing said second section to a second surface of said stretchable member, while said stretchable member is disposed in said extended configuration, such that said second section is subsequently extendible with said stretchable member.

17. The method of claim 14, wherein said stretchable member has a first end and a second end, and wherein said step of positioning said stretchable member includes positioning said first end adjacent said first section, said first section being proximate said front longitudinal end of said first layer and positioning said second end adjacent a second section, said second section being proximate said back longitudinal end of said first layer, said method further comprising the step of securing said second section to a surface of said stretchable member adjacent said second end.

18. The method of claim 17, further comprising the step of:

cutting out an intermediate side section of said web structure through said first layer, second layer, and said stretchable member, said side section being intermediate said longitudinal ends of said first and second layers and intermediate said first and second ends of said stretchable member, to form a mateable pair of stretchable ear portions.

19. The method of claim 14, wherein said stretchable member has a first end and a second end, and wherein said step of positioning said stretchable member includes positioning said first end adjacent said first section, and positioning said second end adjacent a second section of said first layer, wherein said second section is proximate said other lateral edge of said first layer, said method further comprising said step of securing said second section to a surface of said stretchable member adjacent said second end.

20. A disposable absorbent garment comprising:

a layered assembly including
  a topsheet
  a backsheet, and
  an absorbent core disposed between said topsheet and said backsheet, said layered assembly having a first pair of elasticated ear portions and a second pair of elasticated ear portions, each of said first and second pairs of elasticated ear portions being joined to define a waist opening and a pair of leg openings; and wherein each of said ear portions includes
  an ear section of said topsheet having an outside surface
  an ear section of said backsheet having an outside surface, said outside surface of said backsheet having a decorative or instructional printed display thereon, and
  an elastic stretchable non-permanently elongated member disposed between said ear sections and extendible between a contracted condition and an extended, non-permanently elongated condition, said ear sections being secured to said elastic member such that said ear sections are extendible with said elastic member from a contracted configuration to an extended configuration wherein each of said outside surfaces is disposed in a substantially planar configuration substantially corresponding with a configuration taken on by each said outside surface when said garment is worn, such that said display is substantially observable thereon, and wherein said ear sections are secured to said elasticated member when said elastic member is disposed in said extended condition, such that said ear sections are extendible with said elastic member from a contacted configuration, wherein said display is substantially less observable to an extended configuration wherein each of said outer surfaces is returned unaltered to said substantially planar configuration without permanent elongation of said outer material layer and said stretchable non-permanently elongated member.

21. The garment of claim 20, wherein each of said ear sections has an inside surface positioned generally opposite one of said outside surfaces, said inside surface being secured to a corresponding surface of said elastic member.

22. The garment of claim 20, wherein said outside surfaces exhibit gathers when said ear sections are disposed in said contracted configuration.

23. The garment of claim 20, wherein said elastic member includes a heat-activated elastomer that contracts from an initial extended condition upon application of heat, and wherein said ear sections are attached to said elastic member when said heat-activated elastomer is disposed in said initial extended condition.

24. The garment of claim 20, wherein said elastic member is an elongated elastic member having one end disposed in one of said pairs of joined ear portions and a second end disposed in a corresponding one of said other pair of joined ear portions.

25. The garment of claim 20, wherein said elastic member is positioned in said ear portion such that said ear portion is extendible in a direction substantially lateral with respect to said longitudinal plane.

26. The garment of claim 20, wherein said layered assembly includes a front region from which two of said ear portions extend in substantially lateral directions with respect to said longitudinal plane, a back region from which two other of said ear portions extend in substantially lateral directions with respect to said longitudinal plane, and a crotch region disposed between said front region and said back region.

27. A method of making a disposable garment having an elasticated ear portion, said method comprising the steps of:

providing a first layer and a second layer, each layer including a front section having a first pair of ear sections, a back section having a second pair of ear sections, a crotch section extending between said front and back sections, and a longitudinal axis extending substantially centrally between said front section, back section, and crotch section, wherein said pairs of car sections extend substantially laterally respective of said longitudinal axis, wherein each said ear section has an outside surface provided with a display thereon;

providing an absorbent core;

providing an elastic member contractible from an extended configuration to a relaxed configuration;

positioning said elastic member adjacent a first ear section of said first layer;

securing said first ear section to a surface of said elastic member, while said elastic member is disposed in an extended configuration and while an said outside surface of said first ear section is extended so as to be substantially smooth and planar, such that said first ear section is subsequently contractible, wherein said display is substantially less observable and extendible with said stretchable member and returnable to the extended configuration wherein the outer surface is substantially smooth and planar, and substantially unaltered from when the first ear section is initially secured to the elastic member and wherein said display is observable thereon;

positioning said absorbent core centrally adjacent said first layer;

securing said first layer, said second layer and said absorbent core together, such that said longitudinal axes align, to form a composite structure having a front region that includes said front sections and a pair of laterally extending ear portions, a back region that includes said back sections and a pair of laterally extending ear portions, and a crotch region that includes said crotch sections, whereby said elastic member and said first ear section are included in one of said ear portions to form an elasticated ear portion; and joining each of said ear portions of said front region with a corresponding ear portion of said back region to define a waist opening and a pair of leg openings.

28. The method of claim 27, further comprising the step:

cutting out a pair of intermediate sections of said composite structure before said joining step, wherein each of said intermediate sections is located between an ear portion of said front region and a corresponding ear portion of said back region.

29. The method of claim 27, wherein said step of providing an elastic member includes providing an elongated elastic member having a first end and a second end and wherein said step of positioning said elastic member includes positioning said first end adjacent said first ear section of said first layer and positioning said second end adjacent a second ear section of said first layer, said method further comprising the step of:

securing said second ear section to a second surface of said elastic member, while said elastic member is disposed in an extended configuration, such that said second ear section is subsequently contractible and extendible with said elastic member.

* * * * *